(12) United States Patent
Decuzzi et al.

(10) Patent No.: US 8,173,115 B2
(45) Date of Patent: *May 8, 2012

(54) PARTICLE COMPOSITIONS WITH A PRE-SELECTED CELL INTERNALIZATION MODE

(75) Inventors: Paolo Decuzzi, Bari (IT); Mauro Ferrari, Houston, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 390 days.

This patent is subject to a terminal disclaimer.

(21) Appl. No.: 12/181,759

(22) Filed: Jul. 29, 2008

(65) Prior Publication Data

US 2010/0029785 A1 Feb. 4, 2010

(51) Int. Cl.
*A61K 47/48* (2006.01)
(52) U.S. Cl. .................... 424/78.17; 525/54.1; 977/904; 977/962
(58) Field of Classification Search .................... None
See application file for complete search history.

(56) References Cited

U.S. PATENT DOCUMENTS

| | | | |
|---|---|---|---|
| 4,520,110 | A | 5/1985 | Stryer et al. |
| 4,888,176 | A | 12/1989 | Langer et al. |
| 4,933,185 | A | 6/1990 | Wheatley et al. |
| 5,010,167 | A | 4/1991 | Ron et al. |
| 5,651,900 | A | 7/1997 | Keller et al. |
| 5,770,076 | A | 6/1998 | Chu et al. |
| 5,798,042 | A | 8/1998 | Chu et al. |
| 5,893,974 | A | 4/1999 | Keller et al. |
| 5,938,923 | A | 8/1999 | Tu et al. |
| 6,107,102 | A | 8/2000 | Ferrari |
| 6,858,184 | B2 | 2/2005 | Pelrine et al. |
| 7,091,041 | B2 | 8/2006 | Monahan et al. |
| 2003/0114366 | A1 | 6/2003 | Martin et al. |
| 2003/0205552 | A1 | 11/2003 | Hansford et al. |
| 2004/0064050 | A1 | 4/2004 | Liu et al. |
| 2005/0053590 | A1 | 3/2005 | Meininger |
| 2005/0095174 | A1 | 5/2005 | Wolf |
| 2006/0105032 | A1 | 5/2006 | Lynch et al. |
| 2007/0066138 | A1 | 3/2007 | Ferrari et al. |
| 2007/0299340 | A1 | 12/2007 | Liu et al. |
| 2008/0102030 | A1 | 5/2008 | Decuzzi et al. |
| 2008/0206344 | A1 | 8/2008 | Decuzzi et al. |

FOREIGN PATENT DOCUMENTS

| | | |
|---|---|---|
| WO | WO 03/029403 A3 | 4/2003 |
| WO | WO 2007/120248 A2 | 10/2007 |
| WO | WO 2008/021908 A2 | 2/2008 |
| WO | WO 2008/041970 A2 | 4/2008 |
| WO | WO 2008/067049 A2 | 6/2008 |

OTHER PUBLICATIONS

International Search Report and Written Opinion mailed Jun. 3, 2009, in PCT/US2008/071470, 15 pages.
U.S. Appl. No. 12/110,515, filed Apr. 28, 2008, Ferrari et al.
Champion et al., "Making polymeric micro- and nanoparticles of complex shapes," PHAS, Jul. 17, 2007, 104(29):11901-11904.
Champion et al., "Role of target geometry in phagocytosis," PHAS, Mar. 28, 2006, 103(13):4930-4934.
Cohen et al., "Microfabrication of Silicon-Based Nanoporous Particulates for Medical Applications," Biomedical Microdevices, 2003, 5(3):253-259.
Conner et al., "Regulated portals of entry into the cell," Nature, Mar. 6, 2003, 422:37-44.
Decuzzi et al,. "The role of specific and non-specific interactions in receptor-mediated endocytosis of nanoparticles," Biomaterials, 2007, 28:2915-2922.
Decuzzi et al., "A Theoretical Model for the Margination of Particles within Blood Vessels," Annals of Biomedical Engineering, Feb. 2005, 33(2):179-190.
Decuzzi et al., "Adhesion of Microfabricated Particles of Vascular Endothelium: A Parametric Analysis," Annals of Biomedical Engineering, Jun. 2004, 32(6):793-802.
Decuzzi et al., "The adhesive strength of non-spherical particles mediated by specific interactions," Biomaterials, 2006, 27:5307-5314.
Decuzzi et al., "The Effective Dispersion of Nanovectors Within the Tumor Microvasculature," Annals of Biomedical Engineering, 2006, 34(4):633-641.
Decuzzi et al., "The Receptor-Mediated Endocytosis of Nonspherical Particles," Biophysical Journal, May 2008, 94:3790-3797.
Ferrari, Mauro, "Cancer Nanotechnology: Opportunities and Challenges," Nature Reviews, Mar. 2005, 5:1-11.
Ferrari, Mauro, "Nanovector therapeutics," Current Opinion in Chemical Biology, 2005, 9:343-346.
Freund et al., "The role of binder mobility in spontaneous adhesive contact and implications for cell adhesion," Journal of the Mechanics and Physics of Solids, 2004, 52:2455-2472.
Ganong, William F., Review of Medical Physiology, 21st ed. New York: Lange Medical Books/McGraw-Hill Medical Publishing Division, 2003, Table of Contents, 9 pages.
Gao et al., "Mechanics of receptor-mediated endocytosis," PNAS, Jul. 5, 2005, 102(27):9469-9474.
Hanahan et al., "The Hallmarks of Cancer," Cell, Jan. 7, 2000, 100:57-70.

(Continued)

*Primary Examiner* — Daniel C Gamett
(74) *Attorney, Agent, or Firm* — Winstead PC

(57) ABSTRACT

A method of formulating a particle composition having a pre-selected cell internalization mode involves selecting a target cell having surface receptors and obtaining particles that have i) surface moieties, that have an affinity for or are capable of binding to the surface receptors of the cell and ii) a preselected shape, where a surface distribution of the surface moieties on the particles and the shape of the particles are effective for the pre-selected cell internalization mode.

13 Claims, 4 Drawing Sheets

OTHER PUBLICATIONS

Figure 1:
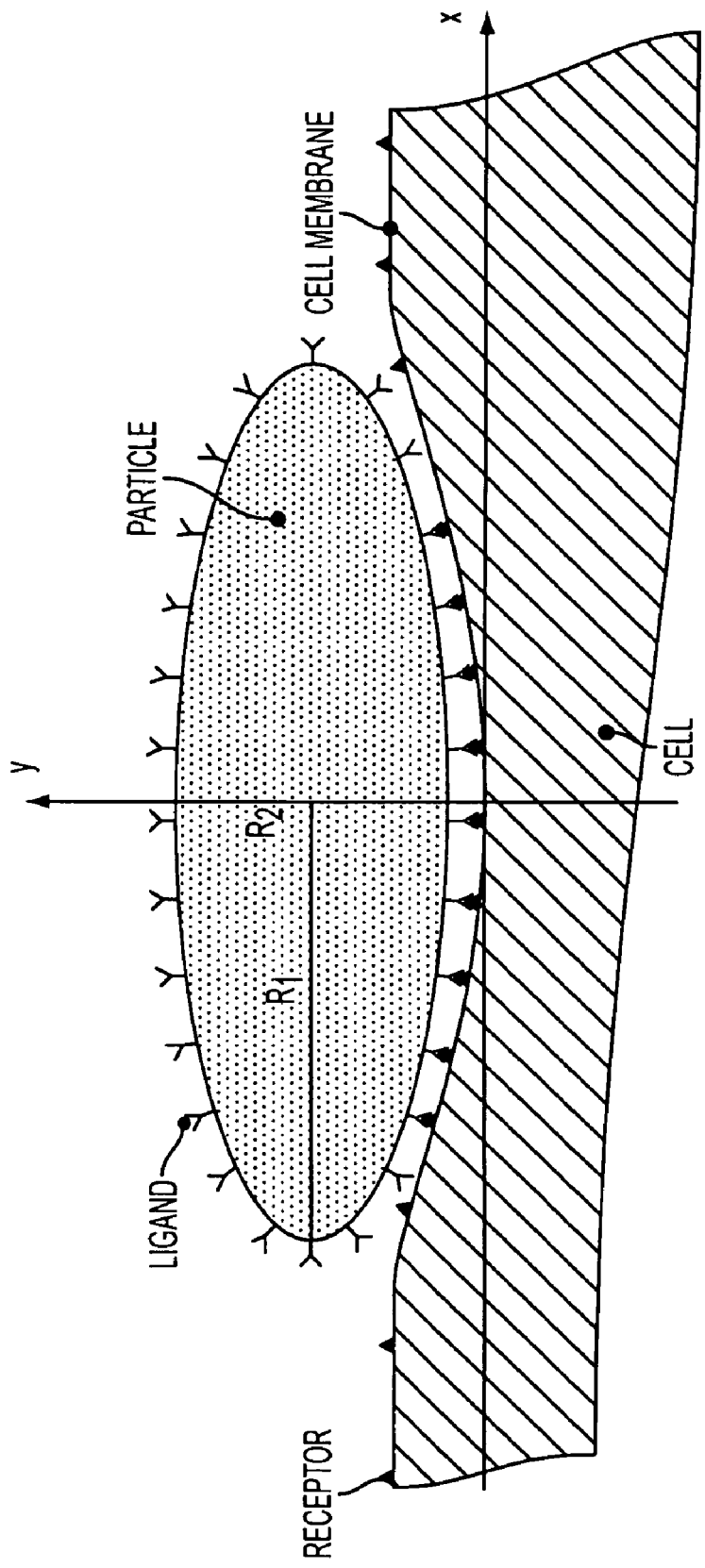

Harris et al., "Influenza virus pleiomorphy characterized by cryoelectron tomography," PNAS, Dec. 12, 2006, 103(50):19123-19127.

Herant et al., "Mechanics of neutrophil phagocytosis experiments and quantitative models," Journal of Cell Science, 2006, 119:1903-1913.

Herant et al., "Mechanics of neutrophil phagocytosis: behavior of the cortical tension," Journal of Cell Science, 2006, 118:1789-1797.

Hill, Terrell L., "An Introcution to Statistical Thermodynamics," 1960, Table of Contents, 5 pages.

Hochmuth, Robert M., "Micropipette aspiration of living cells," Journal of Biomechanics, 2000, 33:15-22.

Marsh et al., "Virus Entry: Open Sesame," Cell, Feb. 24, 2006, 124:729-740.

May et al., "Phagocytosis and the actin cytoskeleton," Journal of Cell Science, Mar. 2001, 114(6):1061-1077.

Mukherjee et al., "Endocytosis," Physiol. Rev., Jul. 1997, 77(3):759-803.

Oberdörster et el., "Nanotoxicology: An Emerging Discipline Evolving from Studies of Ultrafine Particles," Environmental Health Perspectives, Jul. 2005, 113(7):823-839.

Paik et al., "Micromachining of mesoporous oxide films for microelectromechanical system structures," J. Mater. Res., Aug. 2002, 17(8):2121-2129.

Panes et al., "Regional differences in constitutive and induced ICAM-1 expression in vivo," Am. J. Physiol., 1995, 269(6Pt2):H1955-H1964.

Prodan et al., "Low-frequency, low-field dielectric spectroscopy of living cell suspensions," Journal of Applied Physics, Apr. 1, 2004, 95(7):3754-3756.

Rolland et al., "Direct Fabrication and Harvesting of Monodisperse, Shape-Specific Nanobiomaterials," JACS, Jun. 21, 2005, 127:10096-10100.

Simson et al., "Membrane Bending Modulus and Adhesion Energy of Wild-Type and Mutant Cells of *Dictyostelium* Lacking Talin or Cortexillins," Biophysical Journal, Jan. 1998, 74:514-522.

Smith et al., "How Viruses Enter Animal Cells," Science, Apr. 9, 2004, 304:237-242.

Smythe et al., "Actin regulation in endocytosis," Journal of Cell Science, 2006, 119(22):4589-4598.

Sun et al., "Mechanics of Enveloped Virus Entry into Host Cells," Biophysical Journal: Biophsical Letters, 2006, 90:L10-L12.

Tasciotti et al., "Mesoporous silicon particles as a multistage delivery system for imaging and therapeutic applications," Nature Nanotechnology, Mar. 2008, 3:151-157.

Taylor, Richard F., Ed., "Protein Immobilization Fundamentals and Applications," 1991, 109-110.

Vasir et al., "Polymeric nanoparticles for gene delivery," Expert Opin. Drug Delivery, 2006, 3(3):325-344.

PARTICLE COMPOSITIONS WITH A PRE-SELECTED CELL INTERNALIZATION MODE

STATEMENT FOR FEDERALLY FUNDED RESEARCH

This invention was made with government support under Grant No. W31P4Q-07-1-0008, awarded by Defense Advanced Research Projects Agency (DARPA); and under Grant No. NNJ06HE06A, awarded by NASA. The U.S. government has certain rights in the invention.

FIELD

The inventions relate generally to micro and nanosized particle compositions and their applications and, more particularly, to micro and nanosized particle compositions having a particular pre-selected cell internalization mode.

BACKGROUND

Endocytosis is a general term defining processes, by which a cell can import and/or export selected extracellular species, such as molecules, viruses, particles and microorganisms and target them to specific organelles within a cytoplasm. Endocytosis can occur through a variety of pathways including clathrin-mediated and caveole-mediated endocytosis; phagocytosis; clathrin- and caveole-independent endocytosis. A particular endocytosis pathway may depend on the size and nature of the extracellular cargo, see e.g. Conner S. D. and S. L. Schmid. 2003. Nature 422: 37-44. For instance, caveole-mediated endocytosis is assisted by the activation of caveole, plasma membrane invaginations, with a characteristic size of 50-60 nm; clathrin-mediated endocytosis requires the concentration of transmembrane receptors and their bound ligands on the plasma membrane leading to the formation of vesicular cages with a characteristic size up to few hundreds microns (100-500 nm); phagocytosis involves specific cell-surface receptors and signaling cascades with the formation of cell membrane protrusions that eventually envelope the external micrometer cargo (>1 µm). Clathrin- and caveole-independent endocytosis can be associated with the formation of invaginating vesicles smaller than 100 nm.

Particle endocytosis can be of fundamental importance in several fields, such as virology, drug and gene delivery and in nanotoxicology, see e.g. Marsh M. and A. Helenius. 2006. Cell 124:729-40; Vasir J. K., and V. Labhasetwar. 2006. Expert Opin. Drug Deliv. 3:325-344; Oberdorster G., E. Oberdorster, J. Oberdorster. 2005. 113:823-39.

For nanosized particles, both natural, such as enveloped viruses, or artificial, such as biomimetic particulates, the most effective internalization mechanism can be a receptor-mediated endocytosis, in which molecules (ligands) distributed over the particle surface bind to countermolecules (receptors) expressed over the cell membrane, which can eventually bend to invaginate the foreign cargo, see e.g. Marsh M. and A. Helenius. 2006. Cell 124:729-40; Smith A. E., A. Helenius. 2004. Science 304:237-42. These receptors can be collected at the site of invagination by surface diffusion, without which endocytosis would not occur or would occur over a much longer time scale.

SUMMARY

One embodiment provides a method of formulating a particle composition having a pre-selected cell internalization mode, which comprises a) selecting a cell having surface receptors; and b) obtaining particles that have i) surface moieties, that have an affinity for or are capable of binding to the receptors, and ii) a shape, wherein a surface distribution of the surface moieties and the shape are effective for the pre-selected cell internalization mode for the selected cell.

Another embodiment is a method of treating or monitoring a physiological condition comprising administering to a subject in need thereof an effective amount of a particle composition having a pre-selected cell internalization mode.

Yet another embodiment is a particle composition having a pre-selected cell internalization mode.

DRAWINGS

FIG. 1 schematically depicts a particle that has an elliptical cross-section. The particle has ligand molecules on its surface that can interact with receptor molecules on a surface of cell's membrane.

Figure 2:
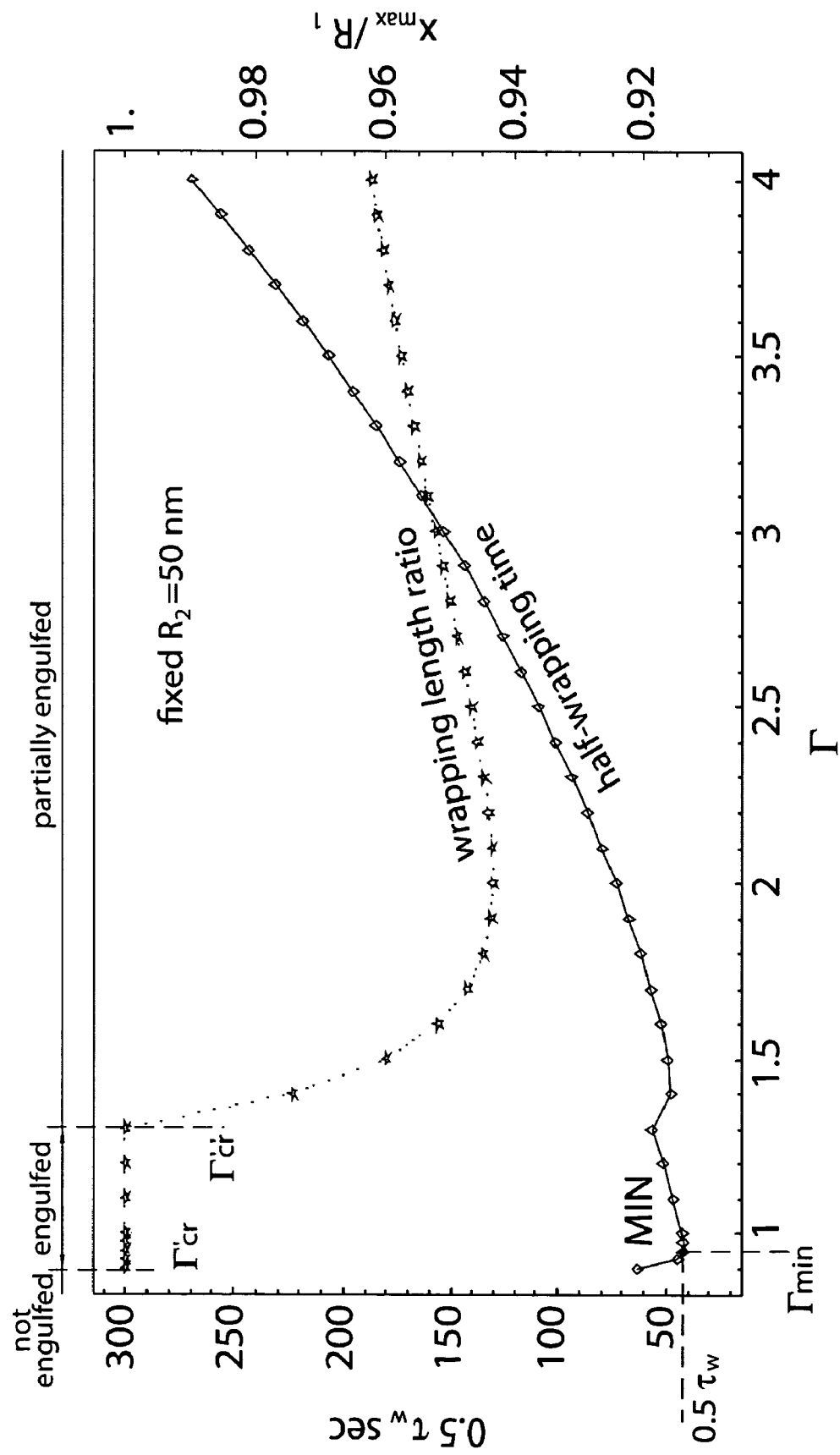

FIG. 2 illustrates evolution of the elliptical cylindrical particle presenting the half-wrapping time $0.5\tau_w$ and the wrapping length ratio $x_{max}/R_1$ as a function of the aspect ratio $\Gamma$, ranging from 0.9 to 4, for $R_2$ fixed at 50 nm.

Figure 3:
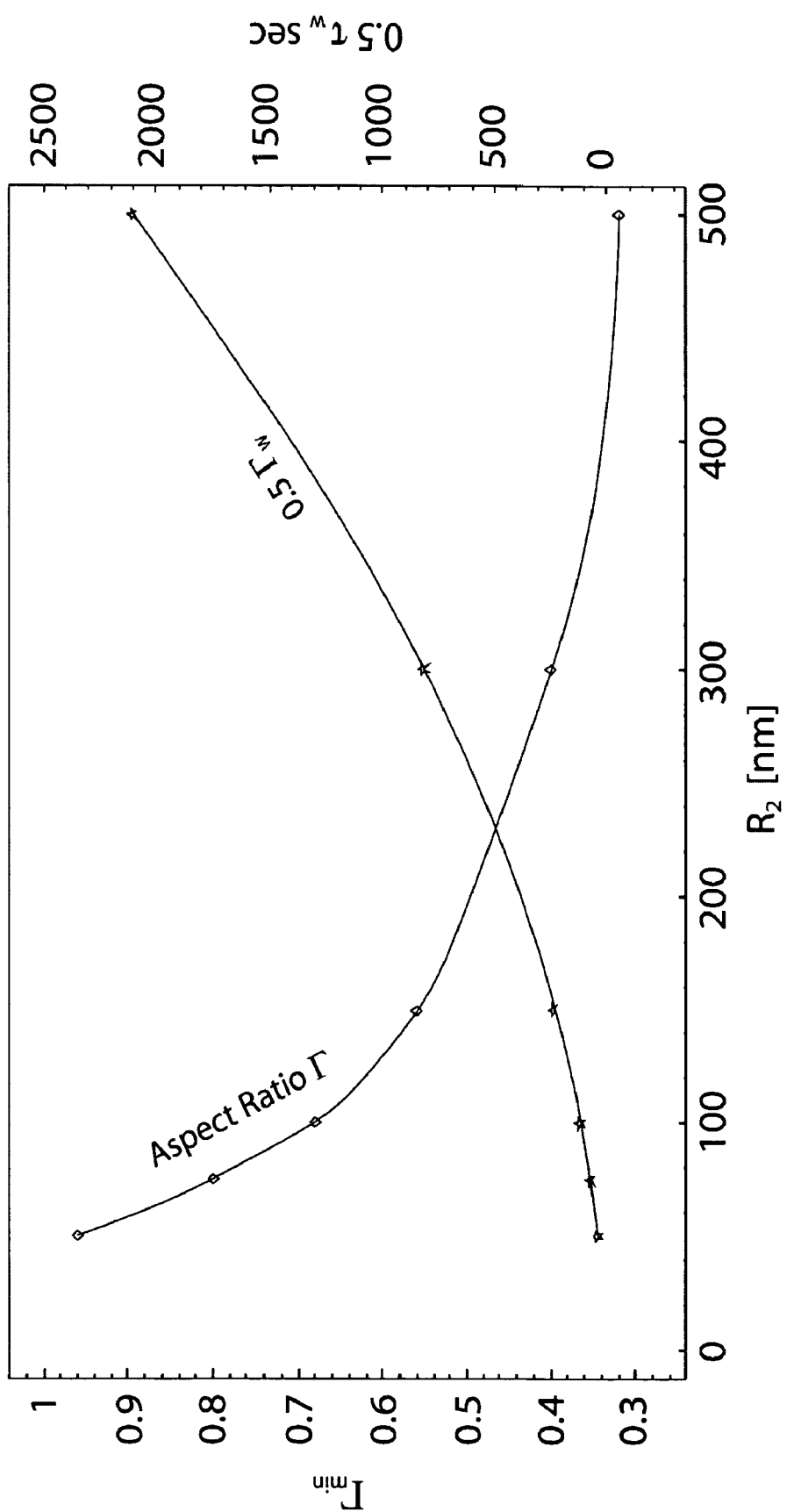

FIG. 3 presents a graph of $\Gamma_{min}$, which is a value of $\Gamma$ for a fixed $R_2$ corresponding to the minimum for the half-wrapping time, as a function of $R_2$. FIG. 3 also presents a graph of the half-wrapping time for $\Gamma_{min}$ as a function of $R_2$.

Figure 4:
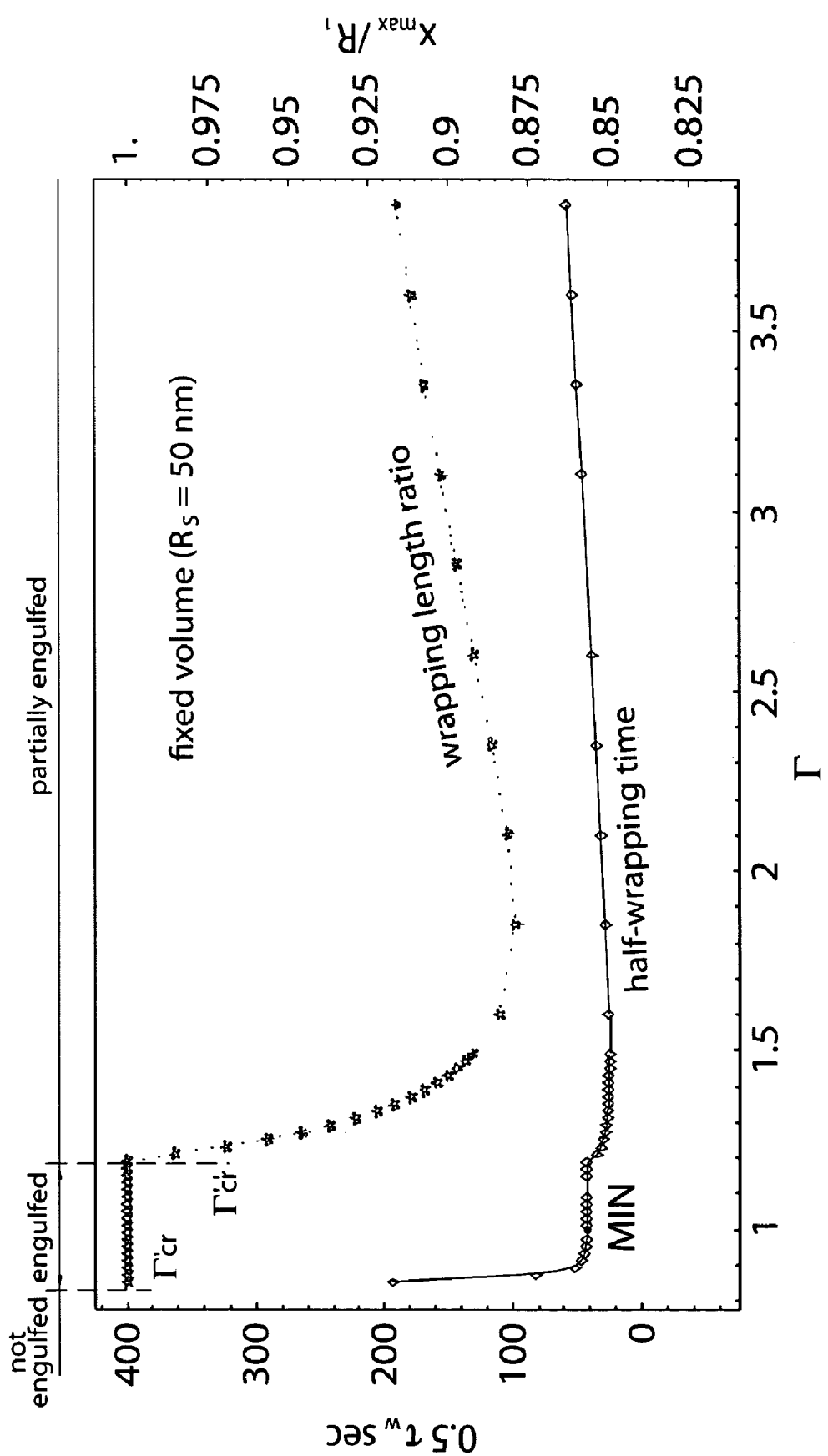

FIG. 4 illustrates evolution of the elliptical cylindrical particle presenting the half-wrapping time $0.5\tau_w$ and the wrapping length ratio $x_{max}/R_1$ as a function of the aspect ratio $\Gamma$, ranging from 0.9 to 4, for a fixed volume ($R_s$=50 nm).

DETAILED DESCRIPTION

Related Documents

The following research articles and patent documents, which are all incorporated herein by reference in their entirety, may be useful for understanding the present inventions:

1) PCT publication no. WO 2007/120248 published Oct. 25, 2007;
2) PCT publication no. WO 2008/041970 published Apr. 10, 2008;
3) PCT publication no. WO 2008/021908 published Feb. 21, 2008;
4) US Patent Application Publication no. 2008/0102030 published May 1, 2008;
5) US Patent Application Publication no. 2003/0114366;
6) U.S. patent application Ser. No. 12/034,259 filed Feb. 20, 2008;
7) U.S. patent application Ser. No. 12/110,515 filed Apr. 28, 2008;
8) Tasciotti et al., Nature Nanotechnology, vol. 3, 151-158, 2008;
9) Decuzzi and Ferrari, Biomaterials 28, 2007, 2915-2922;
10) Decuzzi and Ferrari, Biophysical Journal, 94, 2008, 3790-3797.

Definitions

Unless otherwise specified "a" or "an" means one or more.
Unless otherwise specified the terms "endocytosis" and "endocytotic" mean receptor mediated endocytosis and receptor mediated endocytotic respectively.

"Microparticle" refers to a particle having a maximum dimension from 1 micrometer to 1000 micrometers, or, in some embodiments from 1 micron to 100 microns as specified.

"Nanoparticle" refers to a particle having a maximum dimension of less than 1 micron.

"Phagocytosis" refers to an uptake of large (characteristic size of more than 2 microns) particles by specialized phagocyte cells, which include macrophages, monocytes and neutrophils. Phagocytosis involves the formation of protrusions in the cell membrane that eventually envelope the external particle.

"Receptor mediated endocytosis" or RME refers to an internalization by a cell of a particle, which has moieties, such as ligands, distributed over its surface, which can bind to countermoieties (receptors) expressed over the cell's membrane. RME involves bending of the cell's membrane, which results in a full wrapping of the particle by the membrane and eventual internalization of the particle by the cell. Particles that are internalized via RME can have smaller characteristic size than particles that undergo internalization via phagocytosis. RME is not limited to phagocyte cells.

"Biodegradable" refers to a material that can dissolve or degrade in a physiological medium or a biocompatible polymeric material that can be degraded under physiological conditions by physiological enzymes and/or chemical conditions.

Disclosure

The present inventors recognized an importance of a particle shape for a receptor mediated endocytosis. Accordingly, the present invention provides a method of formulating a particle composition with a pre-selected cell internalization mode, which can involve selecting a target cell and obtaining particles that have on their surfaces surface moieties, that have affinity for or are capable of binding to surface receptors of the surface of the target cell. The surface distribution of the surface moieties on the particles and a shape of the particles are such that they are effective for the pre-selected cell internalization mode for the selected cell.

The pre-selected cell internalization mode may be selected from an "endocytosis" or "no-endocytosis" mode. "Endocytosis" refers to a mode, when a particle can be fully wrapped by the cell's membrane via a receptor mediated endocytosis and eventually internalized, "no-endocytosis" refers to a mode, when the particle can be at most partially wrapped by the cell's membrane.

In some embodiments, the pre-selected cell internalization mode may a frustrated or partial endocytosis. "Frustrated endocytosis" refers to a mode, when the particle gets only partially wrapped by the cell's membrane and does not get internalized by the cell.

The particles with a pre-selected cell internalization mode may be used for treating and/or monitoring a physiological condition. In such a case, one can select a target site, which is affected with the physiological condition and has cells of which have surface receptors on its surface, in a body of a subject, such as a mammal, preferably a human, and administering to the subject an effective amount of a composition that comprises particles with a pre-selected internalization mode for the cells of the target site. The physiological condition can be for example a disease, such as cancer or an inflammation.

In general, the selected cell may be any type of cell that has surface receptors on its surface. In many embodiments, the selected cells can be a mammal cell, such as a human cell.

A particular selected internalization mode may depend on the application intended for the particles. For example, the endocytosis mode may be preferred when the particle contains a cargo, such as an imaging or a therapeutic agent, which is desired to be delivered inside the cell. On the other hand, no endocytosis or frustrated endocytosis modes may be preferred when the particle contains a cargo, which is not intended for delivery inside the cell. One example of such situation can be a multistage delivery vehicle disclosed in PCT publication WO 2008/021908, where a first stage particle of the vehicle, which contains inside second stage particles, is intended to recognize and adhere to a target site in endothelium, without being internalized by the endothelial cells. After adherence, the first stage particle can release the second stage particles.

In many embodiments, the selected cell can be a non-phagocyte cell, i.e. a cell that cannot perform phagocytosis. Examples of phagocyte cells, i.e. cells that perform phagocytosis include neutrophills, monocytes and macrophages.

In some embodiments, the selected cell may be an endothelial cell, such as an endothelial vasculature cell, and the target site may be a vasculature site, such as a coopted vasculature, an angiotensic vasculature or a renormalized vasculature. For cells of coopted vasculature, the surface receptors may be angiopoietin 2 receptors; for cells of angiogenic vasculature, the surface receptors may be vascular endothelial growth factors (VEGF), basic fibroblast growth factors or endothelial markers such as $\alpha_v\beta_3$ integrins; for cells of renormalized vasculature, the surface receptors may be carcinoembionic-related cell adhesion molecules 1 (CEACAM1), endothelin-B receptor (ET-B), vascular endothelial growth factor inhibitors gravin/AKAP12, scaffolding proteins for protein kinase A and protein kinase C.

The surface moieties of the particle's surface can be complimentary to the receptors on the selected cell's surface. The surface moieties may be, for example, antibodies, aptamers or ligands with affinity for or capable of binding to the receptors on the selected cell's membrane surface. In some embodiments, the surface moieties may include specific moieties to the receptors on the selected cell's membrane surface. In some embodiments, the surface moieties may include non-specific moieties to the receptors on the selected cell's membrane surface. Yet in other embodiments, the surface moieties may include both specific and non-specific moieties.

Particles with a pre-selected internalization mode may be a part of a composition that can also include particles without the pre-selected internalization mode. The particles with the pre-selected internalization mode may constitute at least 10% or at least 25% or at least 50% or at least 75% or at least 90% by number of the total number of particles in the composition.

In many embodiments, the particle can be a non-spherical particle. In some embodiments, the particle can be a particle with a circular cross section. In some embodiments, the particle can be an ellipsoidal particle. Yet in other embodiments, the particle can be a cylindrical particle with an elliptical cross section in a direction perpendicular to the axis of the cylinder.

In some embodiments, the particle's largest characteristic size, such as a length of its major axis for a particle with an elliptical cross section, can be less than 2 microns, or less than 1 micron or less than 800 nm or from 5 nm to 500 nm or from 5 nm to 800 nm from 5 nm to 1 micron or from 10 nm to 1 micron or from 10 nm to 800 nm or from 10 nm to 500 nm or from 20 nm to 1 micron or from 20 nm to 800 nm or from 20 nm to 500 nm or from 50 nm to 1 micron or from 50 nm to 800 nm or from 50 nm to 500 nm.

Preferably, the particle's largest characteristic size is substantially smaller than a characteristic size of the selected cell. The particle's largest characteristic size can be at least 3 times smaller or at least 5 times smaller or at least 10 times smaller or at least 20 times smaller or at least 30 times smaller or at least 50 times smaller or at least 100 times smaller or at least 200 times smaller or at least 300 times smaller or at least 500 times smaller or at least 100 times smaller than the characteristic size of the selected cell. A characteristic size of the selected cell may vary from about 5 microns to about 40 microns or from about 10 microns to about 30 microns.

In some embodiments, the obtained particles may be particles that have a convex subsurface with a local curvature and a local surface density of the moieties, such as ligands, that are effective for internalization of the particles via a receptor mediated endocytosis, which means that the local curvature κ is smaller than a maximum endocytosis curvature $\kappa_{max}$ for the local surface density of the moieties. Maximum endocytosis curvature can depend on a binding energy between moieties on the surface of the particle and receptors on the surface of the selected cell's membrane, a bending energy factor of the selected cell's membrane and surface densities of the moieties of the particle and of the receptors on the selected cell's membrane. Methods of evaluating maximum endocytosis curvature are disclosed below.

In some embodiments, the local surface density of the moieties at the convex surface may be greater than a surface density of the moieties at other parts of the surface of the particle, thus, making a surface distribution of the surface moieties on the surface of the particle non-uniform.

For particles with an elliptical cross section, obtaining particles with a pre-selected cell internalization mode may involve obtaining particles that have an aspect ratio corresponding to the selected mode.

For example, FIG. 1 illustrates a elliptical cross section of an elliptical cylindrical particle that interacts with a membrane via specific ligand receptor bonds. A surface density of the ligands on the surface of the particle is $m_l$, while the surface density of the receptors on a surface of the cell's membrane is $m_r$.

The elliptical cross section can be characterized $R_1$ and $R_2$, which are semi-lengths of the axes of the ellipse. An aspect ratio of the ellipse, which can be defined as $\Gamma=R_1/R_2$. The cross sectional area of the particle is $A=\pi R_1 R_2 = \pi \Gamma R_2^2 = \pi R_s^2$, where $R_s$ is a radius of a particle with a circular cross-section that has the same are as the elliptical particle.

The geometry of the particle can be fully defined by a number of pairs of parameters such $R_1$ and $R_2$; $\Gamma$ and $R_1$; $\Gamma$ and $R_2$, $\Gamma$ and $R_s$ or $\Gamma$ and V, where V is the volume of the particle.

In a case, when the geometry of the particle is defined through $\Gamma$ and $R_2$, a shape parameter determining a pre-selected internalization mode can be an aspect ratio $\Gamma$ for a particular $R_2$.

The particle with an elliptical cross section can be in a "no-endocytosis" mode if the aspect ratio of the particle for a particular semilength of a minor axis is less than a first critical value $\Gamma'=(R_2 \kappa_{max})^{-1/2}$, where $\kappa_{max}$ is a maximum endocytosis curvature, which is defined below.

The particle can be in a frustrated endocytosis mode if the aspect ratio of the particle for a particular semilength of its minor axis is no greater than a second critical value, $\Gamma''=R_2 \kappa_{max}$.

The particle can be in an endocytosis mode if the aspect ratio of the particle for a particular semilength of its minor axis is greater than the first critical value, $\Gamma'$, and less than the second critical value, $\Gamma''$.

The maximum endocytosis curvature $\kappa_{max}$ can be defined as an inverse minimum endocytotic radius calculated for the selected cell for a spherical particle or a particle with a circular cross section that has the same ligands on its surface as the non-spherical particle.

The minimum endocytotic radius and thus the maximum endocytotic curvature can be evaluated using the formula (1)

$$\kappa_{max}^{-1} = R_{min} = \sqrt{\frac{B}{2m_l}} \Big/ \sqrt{C - \frac{m^r}{m_l} + \log\frac{m_r}{m_l} + 1} \tag{1}$$

In the equation above, C is the ligand-receptor binding energy relative to $k_B T$, where $k_B$ is the Bolzmann's constant and T is a temperature of the cell or the target site expressed in Kelvins (absolute temperature). C depends on a particular ligand-receptor pair. In particular, $C=\log[K_d^{2D}]$, $K_d^{2D}$ is an equilibrium dissociation constant for the ligand-receptor interacting at the cell/particle interface. $K_d^{2D}$ can be estimated from the following relation $K_d^{2D}=K_d/h$, where $K_d$ is an equilibrium dissociation constant for the same ligand-receptor pair determined, for example, experimentally in solution and h is a thickness of a confinement region, to which the ligand-receptor sites are restricted. In many cases, h can be equal approximately to 10 nm.

B is a bending energy factor of the cell's membrane, which can be determined as detailed in Hochmuth, R. M., J. Biomech., 33:15-22, 2000.

$m_r$, which is an average surface density on the receptors, when the particle is not interacting with the cell, can be determined using methods known to those of ordinary skill in the art. For example, one can determine $m_r$ in vivo by using radiolabeled monoclonal antibodies complimentary to the receptors as detailed for intercellular adhesion molecule 1 receptors in Panes J., et al. Am. J. Physiol. 1995; 269(6Pt2): H1955-64. Alternatively, $m_r$ can be determined using fluorescently labeled monoclonal antibodies complementary to the receptors. Such fluorescently labeled monoclonal antibodies can be antibodies labeled with phycoerythrin disclosed in U.S. Pat. No. 4,520,110.

$m_l$ is a local surface density of ligands $m_l$, which can be varied by controlling surface functionalization conditions for the particle and/or by varying a size of the ligand molecule. The actual surface density of ligands on the particle can be verified experimentally using citofluometry or radiolabeled countermolecules in radioassays.

For a particle with a uniform surface distribution of ligands, the local surface density and the average surface density can be the same.

In certain embodiments, the minimum endocytotic radius and thus the maximum endocytotic curvature can be evaluated as disclosed in U.S. patent application Ser. No. 12/034,259 "Endocytotic particles" filed Feb. 20, 2008, which is incorporated herein by reference in its entirety.

FIG. 2 illustrates evolution of the elliptical cylindrical particle presenting the half-wrapping time $0.5\tau_w$ and the wrapping length ratio $x_{max}/R_1$ as a function of the aspect ratio $\Gamma$, ranging from 0.9 to 4, for $R_2=50$ nm evaluated using a theoretical model disclosed in Decuzzi and Ferrari, Biophysical Journal, 94, 2008, 3790-3797, which is incorporated herein by reference in its entirety. $x_{max}$ is a projection of the particle's wrapping length over the x-axis in FIG. 1. For $x_{max}/R_1=1$ complete wrapping occurs at time $\tau_w$. In FIG. 2, for $\Gamma<\Gamma'_{cr}$ which about 0.9 in this case, wrapping cannot even start leading to infinitely large $\tau_w$ and null ratio $x_{max}/R_1$. For intermediate values of $\Gamma$, $\Gamma'_{cr}<\Gamma<\Gamma''_{cr}$, the ratio $x_{max}/R_1$ is always unit meaning that complete internalization of the particle occurs, and $0.5\tau_w$ grows with $\Gamma$ almost linearly. For $\Gamma > \Gamma''_{cr}$, $x_{max}/R_1$ decreases, reaches a minimum and then increases steadily with increasing $\Gamma$.

FIG. 3 presents a graph of $\Gamma_{min}$, which is a value of $\Gamma$ for a fixed $R_2$ corresponding to the minimum for the half-wrapping time, as a function of $R_2$. FIG. 3 also presents a graph of the half-wrapping time for $\Gamma_{min}$ as a function of $R_2$. The same date is presented in Table 1, together with $\Gamma'$ and $\Gamma''_{cr}$.

TABLE 1

| $R_2$, nm | $\Gamma_{min}$ | $(0.5\tau_w)_{min}$, sec | $\Gamma'_{cr}$ | $\Gamma''_{cr}$ |
|---|---|---|---|---|
| 38.35 (=$R_{min}$) | 1 | ∞ | 1 | 1 |
| 50 | 0.96 | 41.60 | 0.87 | 1.30 |
| 75 | 0.80 | 78.33 | 0.71 | 1.95 |
| 100 | 0.68 | 123.4 | 0.62 | 2.61 |
| 150 | 0.56 | 243.7 | 0.50 | 3.91 |
| 300 | 0.40 | 823.6 | 0.36 | 7.82 |
| 500 | 0.32 | 2105.2 | 0.28 | 13.0 |

As the particle size $R_2$ grows, the aspect ratio $\Gamma_{min}$, for which the internalization time is the smallest, reduces from 1 ($R_2 = R_{min}$) to 0.3 ($R_2 = 500$ nm).

In some cases, the two parameters describing the geometry of the elliptical cylindrical particle may be $\Gamma$ and $R_s$.

In such a case, a shape parameter determining a pre-selected cell internalization mode can be an aspect ratio $\Gamma$ for a particular value of $R_s$.

The particle with an elliptical cross section can be in a "no-endocytosis" mode if the aspect ratio of the particle for a particular semilength of a minor axis is less than a first critical value $\Gamma'_1 = (R_s \kappa_{max})^{-2/3}$, where $\kappa_{max}$ is a maximum endocytosis curvature, which is defined below.

The particle can be in a frustrated endocytosis mode if the aspect ratio of the particle for a particular semilength of its minor axis is no greater than a second critical value, $\Gamma''_1 = (R_s \kappa_{max})^{2/3}$.

The particle can be in an endocytosis mode if the aspect ratio of the particle for a particular semilength of its minor axis is greater than the first critical value, $\Gamma'_1$, and less than the second critical value, $\gamma''_1$.

FIG. 4 illustrates evolution of the elliptical cylindrical particle presenting the half-wrapping time $0.5\tau_w$ and the wrapping length ratio $x_{max}/R_1$ as a function of the aspect ratio $\Gamma$, ranging from 0.9 to 4, for $R_s = 50$ nm evaluated using a theoretical model disclosed in Decuzzi and Ferrari, Biophysical Journal, 94, 2008, 3790-3797, which is incorporated herein by reference in its entirety.

Types of Particles

A type of a particle with a pre-selected internalization mode is not particularly limiting. For example, the particle may be a liposome, a polymer-based particle, a silicon-and silica based particle, a quantum dot, a gold nanoshell, a dendrimer or a viral particle.

In some embodiments, particles may be fabricated with a shape effective for a pre-selected internalization mode. Yet in some embodiments, particles having a shape effective for a pre-selected internalization mode may be selected from a pool of particles, which may have a broad distribution of shapes and/or sizes. The selection from the pool of particles may be performed, for example, using Zetasizer™ Nano series instrument from Malvern Instruments, Worcestershire, United Kingdom, which allows measuring geometrical dimensions of the particles.

Particles may be fabricated using a number of methods. In general, fabrication methods that provide a control of the size and shape of the particles may be preferred.

In some embodiments, the particles may be fabricated by top-down microfabrication or nanofabrication methods, such as photolithography, electron beam lithography, X-ray lithography, deep UV lithography or nanoprint lithography. The advantage of using the top-down fabrication methods can be that such methods may provide for a scaled up production of particles that are uniform in dimensions.

The particles may have on their surfaces targeting moieties, such as ligands, aptamers or antibodies. For example, ligands may be chemically linked to appropriate reactive groups on the surface of the particles. Protein ligands may be linked to amino- and thiol-reactive groups under conditions effective to form thioether or amide bonds respectively. Methods for attaching antibody or other polymer binding agents to an inorganic or polymeric support are detailed, for example, in Taylor, R., Ed., Protein Immobilization Fundamentals and Applications, pp. 109110 (1991).

Non-uniform surface distribution of surface moieties can be achieved, for example, when making particles by top-down microfabrication or nanofabrication methods. For example, a substrate, from which the particles are made, may be patterned using a coating that resists ligands deposition, so that the particle has at least two different surface areas: one that is resistant to ligand deposition and one that is not. Subsequent exposure of the substrate to a solution containing a ligand may result in particles having non-uniform distribution of ligands upon their release from the substrate.

In some embodiments, the particle may have one or more channels connecting a reservoir with the surface. In some embodiments, the reservoir and the channels may be pores in the body of the particle. In such case, the particle may comprise a porous or nanoporous material. The pores of the porous or nanoporous material may be controlled to achieve a desired load of the active agent and/or a desired release rate. The nanoporous material with controllable pore size may be an oxide material, such as $SiO_2$, $Al_2O_3$, or $TiO_2$. Fabrication of nanoporous oxide particles, also known as sol gel particles, is detailed, for example, in Paik J. A. et. al. J. Mater. Res., Vol. 17, August 2002. The nanoporous material with controllable pore size may be also nanoporous silicon. For details of fabrication of nanoporous silicon particles, see, for instance, Cohen M. H. et. al. Biomedical Microdevices 5:3, 253-259, 2003.

In some other embodiments, the particle may have no channels at all. Such particle may comprise, for example, a biodegradable material. For example, the particle may be formed of metals, such as iron, titanium, gold, silver, platinum, copper, and alloys and oxides thereof. The biodegradable material may be also a biodegradable polymer such as polyorthoesters, polyanhydrides, polyamides, polyalkylcyanoacrylates, polyphosphazenes, and polyesters. Exemplary biodegradable polymers are described, for example, in U.S. Pat. Nos. 4,933,185, 4,888,176, and 5,010,167. Specific examples of such biodegradable polymer materials include poly(lactic acid), polyglycolic acid, polycaprolactone, polyhydroxybutyrate, poly(N-palmitoyl-trans-4-hydroxy-L-proline ester) and poly(DTH carbonate).

In certain embodiments, the particle may be an active agent per se.

Active Agent

The active agent may be a therapeutic compound and/or an imaging agent. The selection of a particular active agent depends on the desired application.

The therapeutic agent may be a physiologically or pharmacologically active substance that can produce a desired biological effect in fenestrated vasculature of the subject, such as a mammal or a human. The therapeutic agent may be an inorganic or organic compound, including peptides, proteins, nucleic acids, and small molecules. The therapeutic agent may be in various forms, such as an unchanged molecule, molecular complex, pharmacologically acceptable salt, such as hydrochloride, hydrobromide, sulfate, laurate, palmitate, phosphate, nitrite, nitrate, borate, acetate, maleate, tartrate, oleate, salicylate, and the like. For an acidic therapeutic agent, salts of metals, amines or organic cations, for example, quaternary ammonium, may be used. Derivatives of drugs, such as bases, esters and amides also may be used as a therapeutic agent. A therapeutic agent that is water insoluble may be used in a form that is a water soluble derivative thereof, or as a base derivative thereof, which in either instance, or by its delivery, is converted by enzymes, hydrolyzed by the body pH, or by other metabolic processes to the original therapeutically active form.

The therapeutic agent may be a chemotherapeutic agent, an immunosuppressive agent, a cytokine, a cytotoxic agent, a nucleolytic compound, a radioactive isotope, a receptor, and a pro-drug activating enzyme, which may be naturally occurring or produced by synthetic or recombinant methods, or any combination thereof.

Drugs that are affected by classical multidrug resistance, such as vinca alkaloids (e.g., vinblastine and vincristine), the anthracyclines (e.g., doxorubicin and daunorubicin), RNA transcription inhibitors (e.g., actinomycin-D) and microtubule stabilizing drugs (e.g., paclitaxel) may have a particular utility as the therapeutic agent.

A cancer chemotherapy agent can be also a preferred therapeutic agent. Useful cancer chemotherapy drugs include nitrogen mustards, nitrosorueas, ethyleneimine, alkane sulfonates, tetrazine, platinum compounds, pyrimidine analogs, purine analogs, antimetabolites, folate analogs, anthracyclines, taxanes, vinca alkaloids, topoisomerase inhibitors and hormonal agents. Exemplary chemotherapy drugs are Actinomycin-D, Alkeran, Ara-C, Anastrozole, Asparaginase, BiCNU, Bicalutamide, Bleomycin, Busulfan, Capecitabine, Carboplatin, Carboplatinum, Carmustine, CCNU, Chlorambucil, Cisplatin, Cladribine, CPT-11, Cyclophosphamide, Cytarabine, Cytosine arabinoside, Cytoxan, Dacarbazine, Dactinomycin, Daunorubicin, Dexrazoxane, Docetaxel, Doxorubicin, DTIC, Epirubicin, Ethyleneimine, Etoposide, Floxuridine, Fludarabine, Fluorouracil, Flutamide, Fotemustine, Gemcitabine, Herceptin, Hexamethylamine, Hydroxyurea, Idarubicin, Ifosfamide, Irinotecan, Lomustine, Mechlorethamine, Melphalan, Mercaptopurine, Methotrexate, Mitomycin, Mitotane, Mitoxantrone, Oxaliplatin, Paclitaxel, Pamidronate, Pentostatin, Plicamycin, Procarbazine, Rituximab, Steroids, Streptozocin, STI-571, Streptozocin, Tamoxifen, Temozolomide, Teniposide, Tetrazine, Thioguanine, Thiotepa, Tomudex, Topotecan, Treosulphan, Trimetrexate, Vinblastine, Vincristine, Vindesine, Vinorelbine, VP-16, and Xeloda.

Useful cancer chemotherapy drugs also include alkylating agents, such as Thiotepa and cyclosphosphamide; alkyl sulfonates, such as Busulfan, Improsulfan and Piposulfan; aziridines, such as Benzodopa, Carboquone, Meturedopa, and Uredopa; ethylenimines and methylamelamines, including altretamine, triethylenemelamine, trietylenephosphoramide, triethylenethiophosphaoramide and trimethylolomelamine; nitrogen mustards, such as Chlorambucil, Chlornaphazine, Cholophosphamide, Estramustine, Ifosfamide, mechlorethamine, mechlorethamine oxide hydrochloride, Melphalan, Novembiehin, Phenesterine, Prednimustine, Trofosfamide, uracil mustard; nitroureas, such as Cannustine, Chlorozotocin, Fotemustine, Lomustine, Nimustine, and Ranimustine; antibiotics, such as Aclacinomysins, Actinomycin, Authramycin, Azaserine, Bleomycins, Cactinomycin, Calicheamicin, Carabicin, Carminomycin, Carzinophilin, Chromoinycins, Dactinomycin, Daunorubicin, Detorubicin, 6-diazo-5-oxo-L-norleucine, Doxorubicin, Epirubicin, Esorubicin, Idambicin, Marcellomycin, Mitomycins, mycophenolic acid, Nogalamycin, Olivomycins, Peplomycin, Potfiromycin, Puromycin, Quelamycin, Rodorubicin, Streptonigrin, Streptozocin, Tubercidin, Ubenimex, Zinostatin, and Zorubicin; anti-metabolites such as Methotrexate and 5-fluorouracil (5-FU); folic acid analogues, such as Denopterin, Methotrexate, Pteropterin, and Trimetrexate; purine analogs, such as Fludarabine, 6-mercaptopurine, Thiamiprine, and Thioguanine; pyrimidine analogs, such as Ancitabine, Azacitidine, 6-azauridine, Carmofur, Cytarabine, Dideoxyuridine, Doxifluridine, Enocitabine, Floxuridine, and 5-FU; androgens, such as Calusterone, Dromostanolone Propionate, Epitiostanol, Rnepitiostane, and Testolactone; anti-adrenals, such as aminoglutethimide, Mitotane, and Trilostane; folic acid replenisher, such as frolinic acid; aceglatone; aldophosphamide glycoside; aminolevulinic acid; Amsacrine; Bestrabucil; Bisantrene; Edatraxate; Defofamine; Demecolcine; Diaziquone; Elfornithine; elliptinium acetate; Etoglucid; gallium nitrate; hydroxyurea; Lentinan; Lonidamine; Mitoguazone; Mitoxantrone; Mopidamol; Nitracrine; Pentostatin; Phenamet; Pirarubicin; podophyllinic acid; 2-ethylhydrazide; Procarbazine; PSK®; Razoxane; Sizofrran; Spirogermanium; tenuazonic acid; triaziquone; 2,2',2"-trichlorotriethylamine; Urethan; Vindesine; Dacarbazine; Mannomustine; Mitobronitol; Mitolactol; Pipobroman; Gacytosine; Arabinoside ("Ara-C"); cyclophosphamide; thiotEPa; taxoids, e.g., Paclitaxel (TAXOL®, Bristol-Myers Squibb Oncology, Princeton, N.J.) and Doxetaxel (TAXOTERE®, Rhone-Poulenc Rorer, Antony, France); Chlorambucil; Gemcitabine; 6-thioguanine; Mercaptopurine; Methotrexate; platinum analogs, such as Cisplatin and Carboplatin; Vinblastine; platinum; etoposide (VP-16); Ifosfamide; Mitomycin C; Mitoxantrone; Vincristine; Vinorelbine; Navelbine; Novantrone; Teniposide; Daunomycin; Aminopterin; Xeloda; Ibandronate; CPT-11; topoisomerase inhibitor RFS 2000; difluoromethylornithine (DMFO); retinoic acid; Esperamicins; Capecitabine; and pharmaceutically acceptable salts, acids or derivatives of any of the above. Also included are anti-hormonal agents that act to regulate or inhibit hormone action on tumors, such as anti-estrogens including for example Tamoxifen, Raloxifene, aromatase inhibiting 4(5)-imidazoles, 4 Hydroxytamoxifen, Trioxifene, Keoxifene, Onapristone, And Toremifene (Fareston); and anti-androgens such as Flutamide, Nilutamide, Bicalutamide, Leuprolide, and Goserelin; and pharmaceutically acceptable salts, acids or derivatives of any of the above.

Cytokines may be also used as the therapeutic agent. Examples of such cytokines are lymphokines, monokines, and traditional polypeptide hormones. Included among the cytokines are growth hormones, such as human growth hormone, N-methionyl human growth hormone, and bovine growth hormone; parathyroid hormone; thyroxine; insulin; proinsulin; relaxin; prorelaxin; glycoprotein hormones, such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin;

thrombopoietin (TPO); nerve growth factors, such as NGF-β; platelet growth factor; transforming growth factors (TGFs), such as TGF-α and TGF-β; insulin-like growth factor-I and -II; erythropoietin (EPO); osteoinductive factors; interferons such as interferon-α, -β and -γ; colony stimulating factors (CSFs), such as macrophage-CSF (M-CSF); granulocyte-macrophage-CSF (GM-CSF); and granulocyte-CSF (GCSF); interleukins (ILs), such as IL-1, IL-1a, IL-2, IL-3, IL-4, IL-5, IL-6, IL-7, IL-8, IL-9, IL-11, IL-12, IL-15; a tumor necrosis factor, such as TNF-α or TNF-β; and other polypeptide factors including LIF and kit ligand (KL). As used herein, the tern cytokine includes proteins from natural sources or from recombinant cell culture and biologically active equivalents of the native sequence cytokines.

The imaging agent may be a substance, that can provide imaging information about a targeted site in a body of an animal, such as a mammal or a human being. The imaging agent can comprise magnetic material, such as iron oxide, for magnetic resonance imaging. For optical imaging, the active agent can be, for example, a semiconductor nanocrystal or quantum dot. For optical coherence tomography imaging, the imaging agent can be a metal, e.g. gold or silver, nanocage particle. The imaging agent can be also an ultrasound contrast agent, such as a micro or nanobubble or iron oxide micro or nanoparticle.

Compositions

The particles having a pre-selected internalization cell mode for particular type of cells can be part of a composition, such as a pharmaceutical composition. Such a composition may be a suspension comprising the particles described above for use in administering a therapeutic or imaging agent. To form the suspension, the particles may be suspended in an aqueous medium at a selected concentration. The optimal concentration can depend on the characteristics (e.g., solubilization properties) of the particle, type of therapeutic application and mode of administration. For example, compositions for oral administration can be relatively viscous, and may therefore contain a higher concentration (e.g., >50%) of the particle. Solutions for bolus injections preferably contain a relatively concentrated suspension of the particles (e.g., 10-50%), but not so concentrated that it has an appreciably higher viscosity than saline (to minimize need for large-bore needles). The solution used for continuous intravenous infusion typically can contain a relatively low concentration (e.g., 2-10% suspension) of the particles, due to the relatively large volumes of fluid that are administered.

The particles may be suspended in a number of suitable aqueous carrier vehicles. A suitable pharmaceutical carrier can be a carrier that is non-toxic to the recipient at the dosages and concentrations employed and is compatible with other ingredients in the formulation. Examples of suitable carrier vehicles include but are not limited to water, saline, Ringer's solution, dextrose solution, and 5% human serum albumin. Suspensions for use in injectable formulations are preferably isotonic with the subject's blood. Generally, the carrier can contain minor amounts of additives, such as substances that enhance isotonicity and chemical stability, e.g., buffers and preservatives, as well as low molecular weight (less than about 10 residues) polypeptides, proteins, amino acids, carbohydrates including glucose or dextrans, chelating agents such as EDTA, or other excipients.

Prior to administration to the subject, the suspension of particles may be sterilized by a suitable sterilization method. Particles fabricated from a heat-stable material may be heat-sterilized, e.g., using an autoclave. Particles fabricated from a not heat-stable material may be sterilized by passage through a commercially-available sterilization filter. Of course, filtration may be used only in cases where the particles is smaller than the pores of the sterilizing filter.

The particles may be administered to a subject in need of therapeutic intervention via a number of suitable administration methods. The particular method employed for a specific application can be determined by the attending physician. For example, the particles may be administered by one of the following routes: topical, parenteral, inhalation, oral, vaginal and anal. Intravascular administration, which includes intravenous (i.v.), intramuscular (i.m.) and subcutaneous (s.c.) injection, may be particularly preferred.

Intravascular administration may be either local or systemic. Local intravascular delivery may be used to bring the particles in the vicinity of a body site having a known tumor or inflammation by use of guided catheter system, such as a CAT-scan guided catheter. General injection, such as a bolus i.v. injection or continuous/trickle-feed i.v. infusion are typically systemic.

The particles may be injected into the blood stream and allowed to circulate and localize to their target site. Preferably, the particles are injected to a vasculature of the target site.

References

1. Gao H, et al. 2005. Proc. Natl. Acad. Sci. USA 102:9469-74.
2. Sun S. X. and D. Wirtz. 2006. Biophysical Journal 90:L10-2.
3. Champion J. A., et al. 2007. Proc. Natl. Acad. Sci. USA 104:11901-4.
4. Champion J. A., S. Mitragotri. 2006. Proc. Natl. Acad. Sci. USA 103:4930-4.
5. Rolland J. P., et al. 2005. J. Am. Chem. Soc. 127:10096-100.
6. Cohen M. H, et al. 2001. Biomedical Microdevices 3:253-259.
7. Harris A, G. et al. 2006. Proc. Natl. Acad. Sci. USA 103: 19123-7
8. Freund L. B. and Y. Lin. 2004. Journal of the Mechanics and Physics of Solids 52:2455-2472
9. Hill T L. 1960. An Introduction to Statistical Thermodynamics. Dover Publications, Inc. New York.
10. Herant M., et al. 2006. J. Cell. Sci. 119: 1903-13.
11. Smythe E., K. R. Ayscough. 2006. J. Cell Sci. 119: 4589-98.
12. May R. C., L. M. Machesky. 2001. J. Cell Sci. 114: 1061-77.
13. Simson R, et al. 1998. Biophysical Journal. 74: 514-522.
14. Herant M, et al. 2005. J. Cell Sci. 118:1789-97.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A method of formulating a particle composition having a preselected cell internalization mode, comprising:
   a) selecting a cell having surface receptors; and
   b) fabricating ellipsoidal particles that have i) surface moieties that have an affinity for or are capable of binding to the receptors, and ii) an aspect ratio that is effective for the preselected cell internalization mode for the selected cell, wherein the pre-selected internalization mode is selected from a full endocytosis, a frustrated endocytosis and no endocytosis.

2. The method of claim 1, wherein the cell is an endothelial cell.

3. The method of claim 2, wherein the endothelial cell is an endothelial vasculature cell.

4. The method of claim 3, wherein the receptors are angiogenesis vasculature receptors, coopted vasculature receptors or renormalized receptors.

5. The method of claim 1, wherein the cell is a non-phagocyte cell.

6. The method of claim 1, wherein the surface moieties are ligands that are capable of binding to the receptors.

7. The method of claim 1, wherein the fabricating comprises fabricating by a top-down process.

8. The method of claim 1, wherein the fabricating comprises disposing the moieties onto a surface of the particles.

9. The method of claim 1, wherein the obtaining comprises selecting the particles from a particle population.

10. The method of claim 1, wherein the particles comprise an active agent.

11. The method of claim 10, wherein the active agent comprises an imaging agent or a therapeutic agent.

12. The method of claim 1, wherein said particles are nanoparticles.

13. The method of claim 1, further comprising determining the aspect ratio based on a surface density of the surface moieties and a surface density of the surface receptors.

* * * * *